United States Patent
Hashimoto et al.

(10) Patent No.: US 10,078,070 B2
(45) Date of Patent: Sep. 18, 2018

(54) AUTOMATED ANALYZER

(75) Inventors: Yoshiaki Hashimoto, Shizuoka (JP); Noriyoshi Okada, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 613 days.

(21) Appl. No.: 13/986,000

(22) PCT Filed: Feb. 17, 2012

(86) PCT No.: PCT/JP2012/001056
§ 371 (c)(1),
(2), (4) Date: Sep. 18, 2013

(87) PCT Pub. No.: WO2012/111343
PCT Pub. Date: Aug. 23, 2012

(65) Prior Publication Data
US 2014/0005952 A1   Jan. 2, 2014

(30) Foreign Application Priority Data
Feb. 17, 2011 (JP) .................... 2011-032332

(51) Int. Cl.
*G01N 30/00* (2006.01)
*G01N 21/31* (2006.01)
(Continued)

(52) U.S. Cl.
CPC .......... *G01N 30/00* (2013.01); *G01N 21/15* (2013.01); *G01N 21/253* (2013.01); *G01N 21/31* (2013.01);
(Continued)

(58) Field of Classification Search
CPC .......... G01N 35/025; G01N 35/1016; G01N 2035/1025; G01N 35/1002; G01N 21/00;
(Continued)

(56) References Cited

U.S. PATENT DOCUMENTS 4,958,295 A * 9/1990 Davidson ............. G01N 35/085
422/67
5,067,616 A * 11/1991 Plester ................. B07C 5/3408
209/3.1
(Continued)

FOREIGN PATENT DOCUMENTS

JP        07-36021 B2    0/1995
JP       2001-091518 A   4/2001
(Continued)

OTHER PUBLICATIONS

Translation of the International Search Report dated Apr. 17, 2012 for PCT Patent Application No. PCT/JP2012/001056, filed on Feb. 17, 2012, 2 pages.
(Continued)

*Primary Examiner* — Roy Y Yi
*Assistant Examiner* — Jeffrey Aiello
(74) *Attorney, Agent, or Firm* — Kilpatrick Townsend & Stockton LLP

(57) ABSTRACT

An analyzer, and a method and an apparatus for detecting liquid overflowing from a container that the analyzer comprises, are provided. The method according to the present invention for detecting liquid overflowing from a container in the analyzer, includes a step of judging that liquid is overflowing from at least one container if the difference between a standard deviation of absorbance of the liquid measured at a plurality of points of a container at time T1 and a standard deviation of absorbance of the liquid measured at a plurality of points in said container at time T2 is greater than a predetermined threshold value.

11 Claims, 6 Drawing Sheets

(51) Int. Cl.
*G01N 21/15* (2006.01)
*G01N 21/25* (2006.01)
*G01N 21/90* (2006.01)
G01N 35/02 (2006.01)
G01N 35/00 (2006.01)

(52) U.S. Cl.
CPC ....... *G01N 21/9018* (2013.01); *G01N 35/025* (2013.01); *G01N 2021/157* (2013.01); *G01N 2035/009* (2013.01); *G01N 2201/0415* (2013.01)

(58) Field of Classification Search
CPC ... G01N 2021/157; B01L 1/00; B01F 9/0001; G01F 25/0092; G01F 23/292
USPC ..... 436/43, 180, 50; 702/19, 22, 85, 55, 23; 73/149, 290, 1.16
See application file for complete search history.

(56) References Cited

U.S. PATENT DOCUMENTS

| | | | |
|---|---|---|---|
| 5,230,863 A * | 7/1993 | Salpeter | G01N 21/274 250/252.1 |
| 6,098,029 A * | 8/2000 | Takagi | G01F 23/292 382/100 |
| 6,723,287 B1 | 4/2004 | Ootatsume et al. | |
| 7,634,378 B2 * | 12/2009 | Kaplit | G01N 35/1016 340/605 |
| 2003/0138961 A1 | 7/2003 | Fava et al. | |
| 2005/0185176 A1 | 8/2005 | Moran et al. | |
| 2007/0107491 A1 * | 5/2007 | Petersen | D21G 9/0027 73/1.16 |
| 2009/0198463 A1 | 8/2009 | Kamihara et al. | |
| 2010/0254857 A1 * | 10/2010 | Mazume | G01N 35/025 422/82.05 |
| 2010/0322822 A1 * | 12/2010 | Fritchie | G01N 35/1009 422/63 |
| 2011/0189715 A1 * | 8/2011 | Likuski | G01N 35/1095 435/29 |
| 2011/0223066 A1 * | 9/2011 | Yamazaki | G01N 21/274 422/82.09 |
| 2011/0257908 A1 * | 10/2011 | Okabayashi | G01N 35/025 702/50 |
| 2012/0064636 A1 * | 3/2012 | Mitsuyama | G01N 35/00623 436/165 |
| 2012/0205299 A1 * | 8/2012 | Darwinkel | C02F 9/005 210/97 |

FOREIGN PATENT DOCUMENTS

| | | |
|---|---|---|
| JP | 2008-209353 A | 9/2008 |
| JP | 2010-151519 A | 7/2010 |
| JP | 2010-160116 A | 7/2010 |
| JP | 2010-243307 A | 10/2010 |
| WO | 2010/079629 A1 | 7/2010 |

OTHER PUBLICATIONS

European Search Report dated Nov. 9, 2017 for EP Patent Application No. 1274797.1, 11 pages.

* cited by examiner

AUTOMATED ANALYZER

CROSS-REFERENCE TO RELATED APPLICATIONS

This application is the U.S. National Stage Entry under § 371 of International Application No. PCT/JP2012/001056, filed Feb. 17, 2012, which claims benefit of priority from Japanese Patent Application No. 2011-032332, filed Feb. 17, 2011, the disclosures of which are incorporated by reference in their entirety.

TECHNICAL FIELD

The present invention relates to: an analyzer, and a method and an apparatus for detecting liquid overflowing from at least one of a plurality of containers that the analyzer comprises.

BACKGROUND ART

Analyzers for dispensing a sample and a reagent into a reaction container and measuring absorbance of a reaction liquid produced in the reaction container to analyze the sample have been conventionally known. Such an analyzer comprises a photometry section having a light source and a light receiving section. The light source irradiates light onto the reaction container containing the reaction liquid, and the light receiving section calculates the absorbance based on the amount of light transmitted through the reaction liquid in the reaction container and received by the light receiving section, to analyze the sample.

One of the methods for calculating absorbance is as follows: every time a reaction container passes through a photometry section, the photometry section successively irradiates light onto a plurality of measurement points on the reaction container, and the photometry section receives the light transmitted through the reaction liquid and averages the received light, thereby calculating the absorbance of the reaction liquid. Through this method, it is possible to prevent variations in the amount of light for each measurement point used to calculate absorbance. However, if there is a measurement point at which a sample and a reagent are not mixed with each other sufficiently, or if there is a measurement point at which a foreign matter or the like is mixed in the reaction liquid, then the light to be transmitted through the reaction liquid is blocked due to such a measurement point. As a result, there have been cases where the amount of light at this measurement point is reduced and absorbance is thus calculated to be a value higher than the actual value.

Thus, another analyzer is known, for excluding absorbance measurement data considered as an erroneous measurement from subjects to be analyzed and conducting an analysis by using only absorbance measurement data having high reliability.

An analyzer for excluding a conspicuous amount of light at a measurement point, different from ordinary amounts of light of chemical reactions at a plurality of measurement points, is described in Patent Document 1, for example.

An analyzer for measuring absorbance data at a plurality of measurement points, calculating an absorbance data change rate with regard to the plurality of measurement points, and excluding absorbance data whose absorbance data change rate is outside the acceptable range, is described in Patent Document 2, for example.

An analyzer for measuring absorbance data at a plurality of measurement points, calculating a standard deviation of an absorbance data change rate regarding the plurality of measurement points, distinguishing a reaction container having a scratch or stain by using the calculated standard deviation, and excluding the absorbance data of the reaction container, is described in Patent Document 3, for example.

These analyzers are for excluding absorbance measurement data considered as erroneous measurements from subjects to be analyzed; however, they are not capable of detecting an overflow of a liquid. Furthermore, with conventional methods for detecting a liquid overflow, it has been necessary to set up an additional detection apparatus.

PRIOR ART DOCUMENTS

Patent Documents

Patent Document 1: Japanese Laid-Open Publication No. 2007-198739
Patent Document 2: Japanese Laid-Open Publication No. 2010-151519
Patent Document 3: Japanese Laid-Open Publication No. 2010-160116

DISCLOSURE OF THE INVENTION

Means for Solving the Problem

The method according to the present invention is a method for detecting liquid overflowing from at least one of a plurality of containers comprised in an analyzer, each container containing liquid, the method comprising the steps of: measuring an absorbance of the liquid contained in one of the plurality of containers at a plurality of points of the one container at a time T1; calculating a standard deviation of the absorbance of the liquid measured at the plurality of points of the one container at the time T1, as a first standard deviation; measuring an absorbance of the liquid contained in the one container at a time T2; calculating a standard deviation of the absorbance of the liquid measured at the plurality of points of the one container at the time T2, as a second standard deviation; judging as to whether or not a difference between the first standard deviation and the second standard deviation is greater than a predetermined threshold value; and judging that the liquid is overflowing from at least one of the plurality of containers if the difference between the first standard deviation and the second standard deviation is greater than the predetermined threshold value, thereby capable of judging that the liquid is overflowing from a container.

The method may further comprise the steps of: measuring an absorbance of the liquid contained in another one of the plurality of containers at a plurality of points of the another container at a time T3; calculating a standard deviation of the absorbance of the liquid measured at the plurality of points of the another container at the time T3, as a third standard deviation; measuring an absorbance of the liquid contained in the another container at a time T4; calculating a standard deviation of the absorbance of the liquid measured at the plurality of points of the another container at the time T4, as a fourth standard deviation; and judging as to whether or not a difference between the third standard deviation and the fourth standard deviation is greater than the predetermined threshold value, wherein the step of judging that the liquid is overflowing from at least one of the plurality of containers, may judge that the liquid is overflowing from at least one of the plurality of containers if the difference between the first standard deviation and the second standard deviation is greater than the predetermined threshold value, and further if the difference between the third standard deviation and the fourth standard deviation is greater than the predetermined threshold value.

The method may further comprise the step of stopping the analyzer if the liquid is judged as overflowing from at least one of the plurality of containers.

The method may further comprise the step of displaying an alarm indicating that the liquid is overflowing if the liquid is judged as overflowing from at least one of the plurality of containers.

The detection apparatus according to the present invention is a detection apparatus for detecting that liquid is overflowing from at least one of a plurality of containers comprised in an analyzer, each container containing the liquid, the detection apparatus comprising: a section for measuring an absorbance of the liquid contained in one of the plurality of containers at a plurality of points of the one container; a section for calculating a standard deviation of the absorbance of the liquid measured at the plurality of points of the one container at the time T1, as a first standard deviation; a section for measuring an absorbance of the liquid contained in the one container at a time T2; a section for calculating a standard deviation of the absorbance of the liquid measured at the plurality of points of the one container at the time T2, as a second standard deviation; a section for judging as to whether or not a difference between the first standard deviation and the second standard deviation is greater than a predetermined threshold value; and a section for judging that the liquid is overflowing from at least one of the plurality of containers if the difference between the first standard deviation and the second standard deviation is greater than the predetermined threshold value, thereby capable of judging that the liquid is overflowing from a container.

The detection apparatus may further comprise: a section for measuring an absorbance of the liquid contained in another one of the plurality of containers at a plurality of points of the another container at a time T3; a section for calculating a standard deviation of the absorbance of the liquid measured at the plurality of points of the another container at the time T3, as third standard deviation; a section for measuring an absorbance of the liquid contained in the another container at a time T4; a section for calculating a standard deviation of the absorbance of the liquid measured at the plurality of points of the another container at the time T4, as a fourth standard deviation; and a section for judging as to whether or not a difference between the third standard deviation and the fourth standard deviation is greater than the predetermined threshold value, wherein the section for judging that the liquid is overflowing from at least one of the plurality of containers, may judge that the liquid is overflowing from at least one of the plurality of containers if the difference between the first standard deviation and the second standard deviation is greater than the predetermined threshold value, and further if the difference between the third standard deviation and the fourth standard deviation is greater than the predetermined threshold value.

The analyzer according to the present invention is an analyzer comprising: a plurality of containers, each containing liquid; a section for analyzing the liquid contained in at least one of the plurality of containers; and a detection apparatus for detecting that liquid is overflowing from at least one of the plurality of containers, wherein the detection apparatus comprises: a section for measuring an absorbance of the liquid contained in one of the plurality of containers at a plurality of points of the one container; a section for calculating a standard deviation of the absorbance of the liquid measured at the plurality of points of the one container at the time T1, as a first standard deviation; a section for measuring an absorbance of the liquid contained in the one container at a time T2; a section for calculating a standard deviation of the absorbance of the liquid measured at the plurality of points of the one container at the time T2, as a second standard deviation; a section for judging as to whether or not a difference between the first standard deviation and the second standard deviation is greater than a predetermined threshold value; and a section for judging that the liquid is overflowing from at least one of the plurality of containers if the difference between the first standard deviation and the second standard deviation is greater than the predetermined threshold value, thereby capable of judging that the liquid is overflowing from a container.

The analyzer may further comprise: a section for measuring an absorbance of the liquid contained in another one of the plurality of containers at a plurality of points of the another container at a time T3; a section for calculating a standard deviation of the absorbance of the liquid measured at the plurality of points of the another container at the time T3, as third standard deviation; a section for measuring an absorbance of the liquid contained in the another container at a time T4; a section for calculating a standard deviation of the absorbance of the liquid measured at the plurality of points of the another container at the time T4, as a fourth standard deviation; and a section for judging as to whether or not a difference between the third standard deviation and the fourth standard deviation is greater than the predetermined threshold value, wherein the section for judging that the liquid is overflowing from at least one of the plurality of containers, may judge that the liquid is overflowing from at least one of the plurality of containers if the difference between the first standard deviation and the second standard deviation is greater than the predetermined threshold value, and further if the difference between the third standard deviation and the fourth standard deviation is greater than the predetermined threshold value.

Effects of the Invention

According to the present invention, it becomes possible to detect liquid overflowing from a container that the analyzer comprises. Furthermore, according to the present invention, it becomes possible to stop the analyzer immediately after the detection of an overflow, and thus preventing damage due to such a liquid overflow. Furthermore, according to the present invention, it becomes possible to notify a user of the liquid overflowing from a container that the analyzer comprises, thus preventing an erroneous report. Furthermore, even if the function according to the present invention is equipped with an analyzer, the initial cost does not have to be increased.

and an abnormal time (right figure: when there is a liquid overflow) in a case when absorbance of liquid contained in a reaction container 20 is measured at eleven points of the reaction container 20 while the reaction container 20 passes through the photometry section 18 once.

Figure 5:
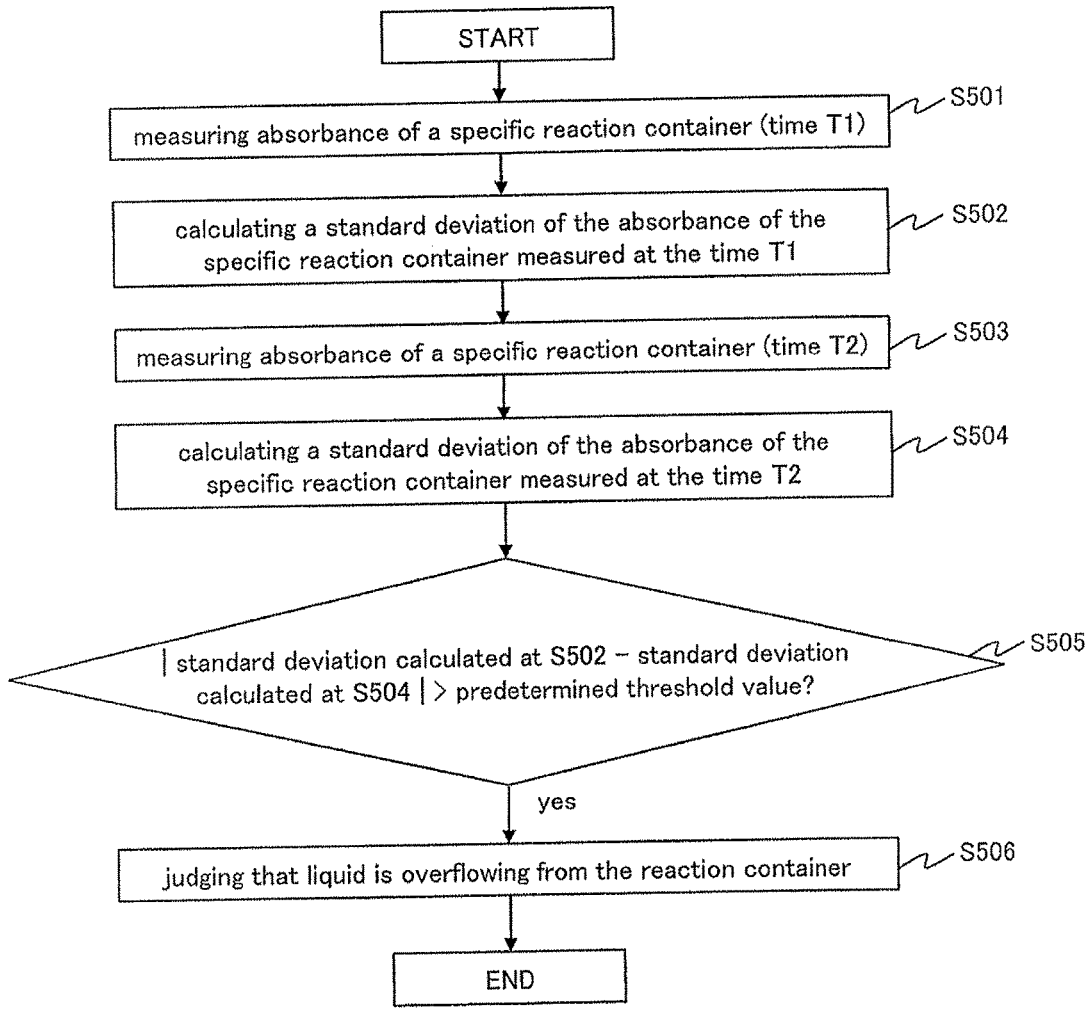

FIG. 5 illustrates an example processing order for detecting an overflow of liquid from at least one of a plurality of reaction containers that an analyzer 1 comprises.

Figure 6:
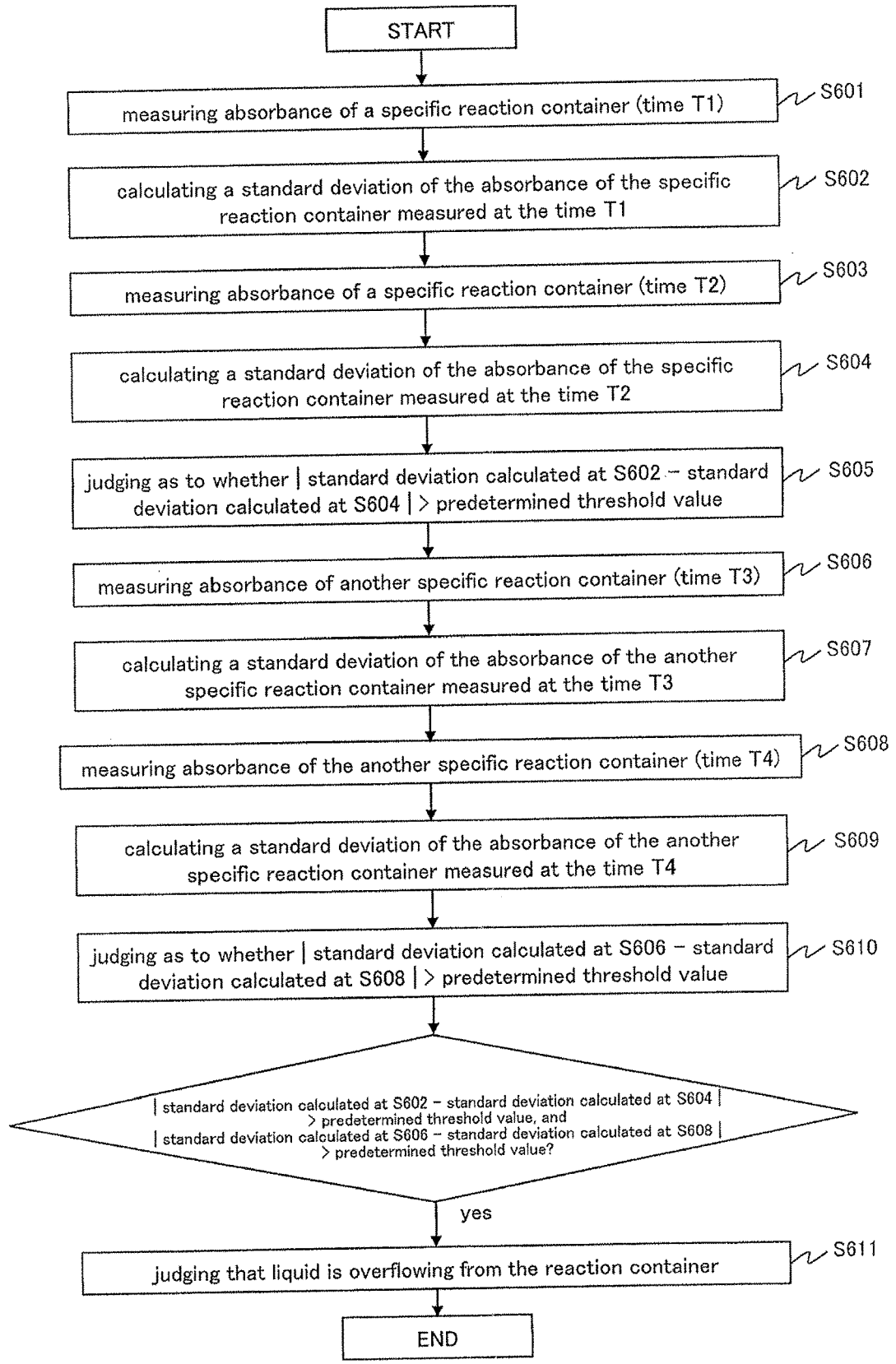

FIG. 6 illustrates another example processing order for detecting an overflow of liquid from at least one of a plurality of reaction containers that the analyzer 1 comprises.

MODES FOR CARRYING OUT THE INVENTION

Hereinafter, embodiments of the present invention will be described with reference to accompanying figures.

Figure 1:
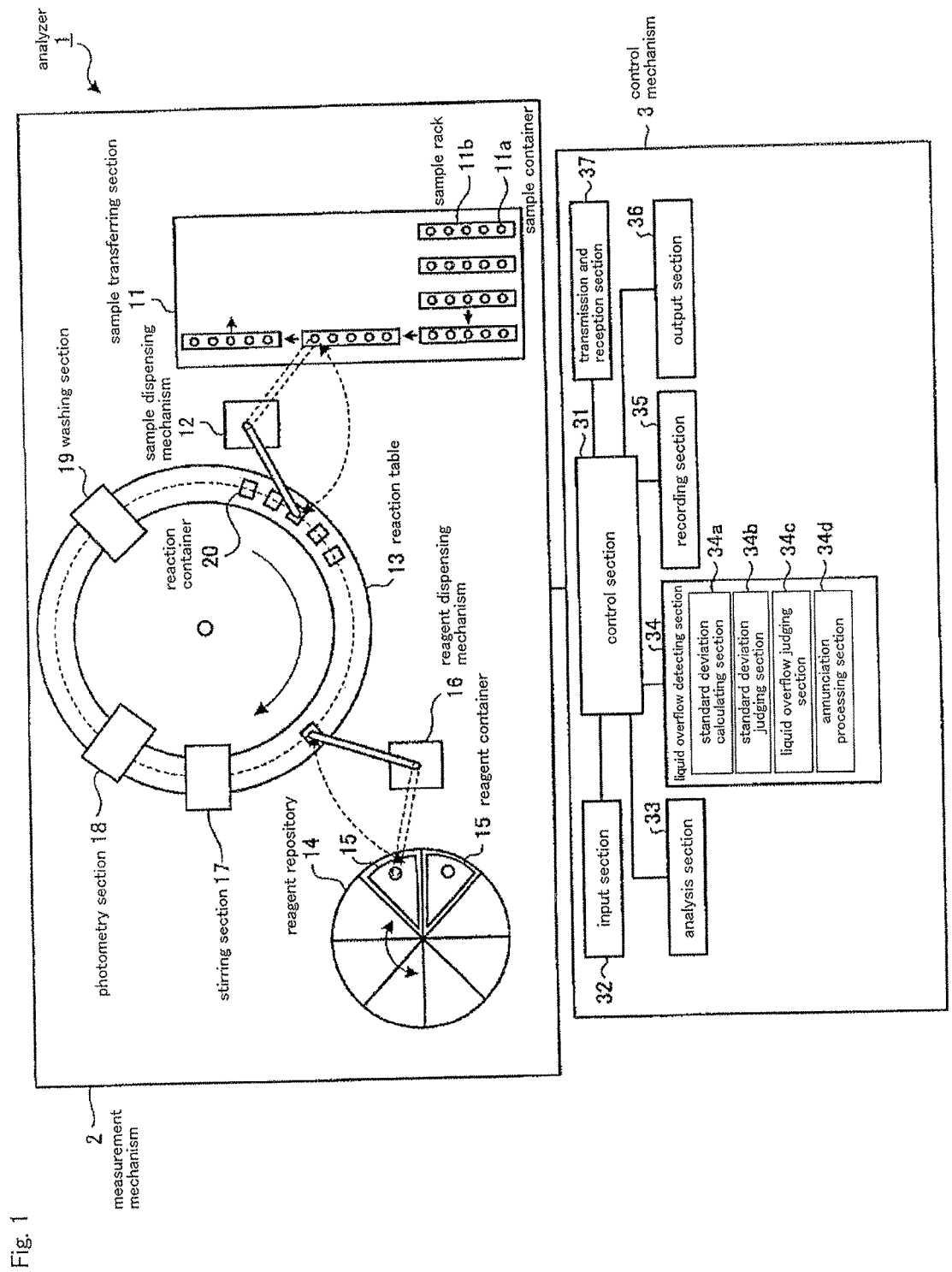
FIG. 1 illustrates an example of a configuration of an analyzer 1 according to an embodiment of the present invention.

FIG. 1 illustrates an example of a configuration of an analyzer 1 according to an embodiment of the present invention. As illustrated in FIG. 1, the analyzer 1 comprises a measurement mechanism 2 for measuring absorbance of a liquid contained in a reaction container 20; and a control mechanism 3 for controlling the overall analyzer 1 including the measurement mechanism 2 and for analyzing a measurement result in the measurement mechanism 2. By the two mechanisms in cooperation with each other, the analyzer 1 automatically performs a detection of a liquid overflowing from a reaction container that the analyzer comprises, and an analysis of the sample.

First, the measurement mechanism 2 will be described. As illustrated in FIG. 1, the measurement mechanism 2 comprises: a sample transferring section 11 for successively transferring a sample rack 11b in the arrowed direction in the figure, where the sample rack 11b retains a plurality of sample containers 11a, each containing a sample such as blood or urine; a sample dispensing mechanism 12 for dispensing, into a reaction container 20, a sample contained in a sample container 11a being at rest at a predetermined position of the sample transferring section 11; a reaction table 13 for retaining a plurality of reaction containers 20 along the circumference, and for rotating in the arrowed direction in the figure to transfer the reaction containers 20 to a predetermined position; a reagent repository 14 for housing a plurality of reagent containers 15 in which a reagent to be dispensed into a reaction container 20 is contained; a reagent dispensing mechanism 16 for dispensing, into a reaction container 20, a reagent contained in a reagent container 15 being at rest at a predetermined position within the regent repository 14; a stirring section 17 for stirring a sample and a reagent dispensed in a reaction container 20; a photometry section 18 for measuring absorbance of a liquid contained in a reaction container 20; and a washing section 19 for washing a reaction container 20.

Next, the control mechanism 3 will be described. The control mechanism 3 comprises: a control section 31; an input section 32; an analysis section 33; a liquid overflow detecting section 34; a recording section 35; an output section 36; and a transmission and reception section 37. The input section 32, analysis section 33, liquid overflow detecting section 34, recording section 35, output section 36 and transmission and reception section 37 are electrically connected with the control section 31.

The control section 31 is realized with a CPU and the like, and the control section 31 controls the processing and operation of respective sections of the analyzer 1. The control section 31 performs given processing on information input from respective constituent sections of the analyzer 1, and also outputs the information, which has been through given processing, to the respective constituent sections.

The input section 32 is realized with a keyboard, a mouse, a touch panel with input and output functions, and the like, and acquires various kinds of information necessary for a sample analysis, instruction information for an analysis operation, and the like from the outside.

The analysis section 33 performs a component analysis of a sample, and the like, based on a measurement result of absorbance measured by the photometry section 18.

The liquid overflow detecting section 34 detects a liquid overflowing from at least one of the reaction containers 20 based on the absorbance of the liquid contained in the reaction containers 20 measured by the photometry section 18, during a washing step of the reaction containers 20. The liquid overflow detecting section 34 comprises: a standard deviation calculating section 34a; a standard deviation judging section 34b; and a liquid overflow judging section 34c. The liquid overflow detecting section 34 may also comprise an annunciation processing section 34d. Every time a reaction container 20 passes through the photometry section 18, the standard deviation calculating section 34a calculates a standard deviation of a plurality of absorbances of the liquid in the reaction container 20 at a plurality of points that are measured by the photometry section 18 while the reaction container 20 passes through the photometry section 18 once. With regard to each specific reaction container among the reaction containers 20, the standard deviation judging section 34b judges as to whether or not the difference (absolute value) between a standard deviation, calculated by the standard deviation calculating section 34a, of a plurality of absorbances of a liquid measured by the photometry section 18 while the reaction container passes through the photometry section 18 once at a certain time, and a standard deviation, calculated by the standard deviation calculating section 34a, of the plurality of absorbances of the liquid measured by the photometry section 18 while the reaction container passes through the photometry section 18 once at a different time, is greater than a predetermined threshold value. In one embodiment, the liquid overflow judging section 34c judges that a liquid is overflowing from at least one of the reaction containers 20 when the standard deviation judging section 34b judges that the difference between the standard deviations is greater than a predetermined threshold value. The annunciation processing section 34d outputs an alarm indicating that a liquid is overflowing, to the output section 36 through the control section 31 when the liquid overflow judging section 34c judges that the liquid is overflowing from at least one of the reaction containers 20.

The recording section 35 is realized with a hard disk for magnetically storing information; and a memory for loading, and electrically storing, various programs from the hard disk when the analyzer 1 performs processing, the programs being associated with the processing. The recording section 35 stores various pieces of information including an analysis result of a sample and the like. The recording section 35 may comprise a supplemental storing apparatus capable of reading information stored on a storage medium, such as CD-ROM, DVD-ROM, PC card and the like.

The output section 36 is realized with a display, a printer, a speaker and the like, for outputting various kinds of information.

The transmission and reception section 37 has a function as an interface for transmitting and receiving information in accordance with a predetermined format via a communication network (not shown).

In the analyzer 1 as configured above, the photometry section 18 measures absorbance of a liquid contained in each reaction container 20 during a washing step of a plurality of reaction containers 20 successively transferred on the reaction table 13, by the washing section 19; and based on this measurement result, the liquid overflow detecting section 34 conducts an analysis. Thus, detection is conducted as to whether a liquid is overflowing from at least one of the reaction containers 20. Furthermore, when a component analysis of a sample or the like is conducted in the analyzer 1 as configured above, the reagent dispensing mechanism 16 dispenses a reagent, from a reagent container 15 of the reagent repository 14, into a plurality of reaction containers 20 successively transferred on the reaction table 13. Subsequently, the sample dispensing mechanism 12 dispenses a sample from a sample container 11a at a sample suction position. Subsequently, the photometry section 18 measures absorbance of a reaction liquid obtained through reaction of the reagent and the sample, and the analysis section 33 conducts an analysis based on the measurement result, thereby conducting a component analysis of a sample or the like automatically. Subsequently, the washing section 19 washes the reaction container 20, which is conveyed after the measurement by the photometry section 18 is completed, while the reaction container 20 is being conveyed.

Figure 2:
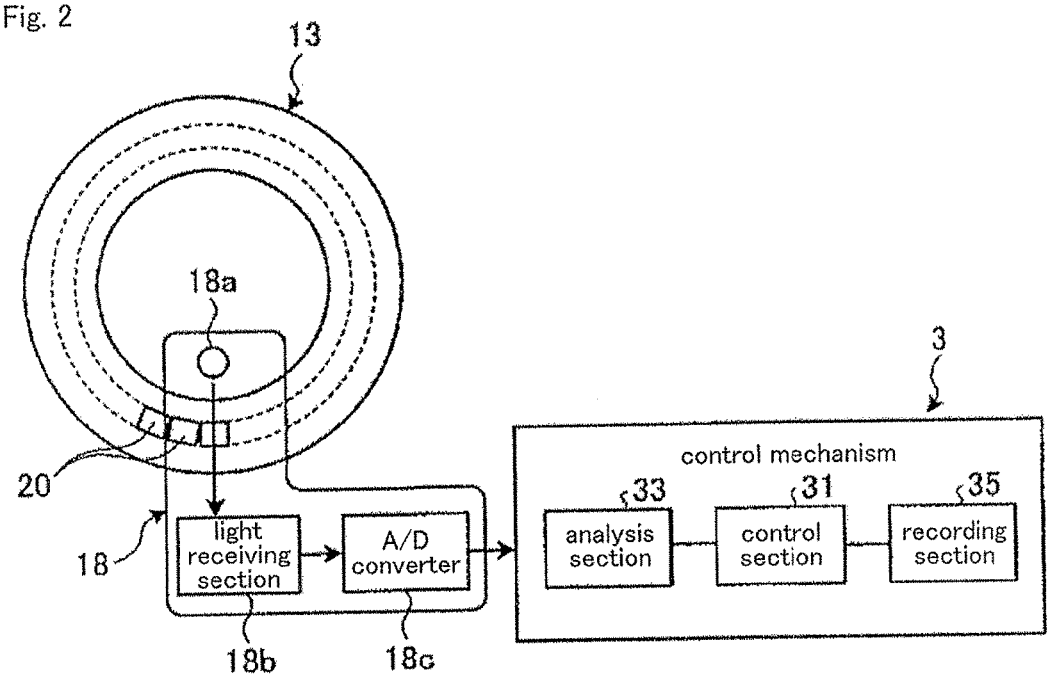
FIG. 2 is a schematic view illustrating a diagrammatic configuration of a photometry section 18 according to an embodiment of the present invention.
Figure 3:
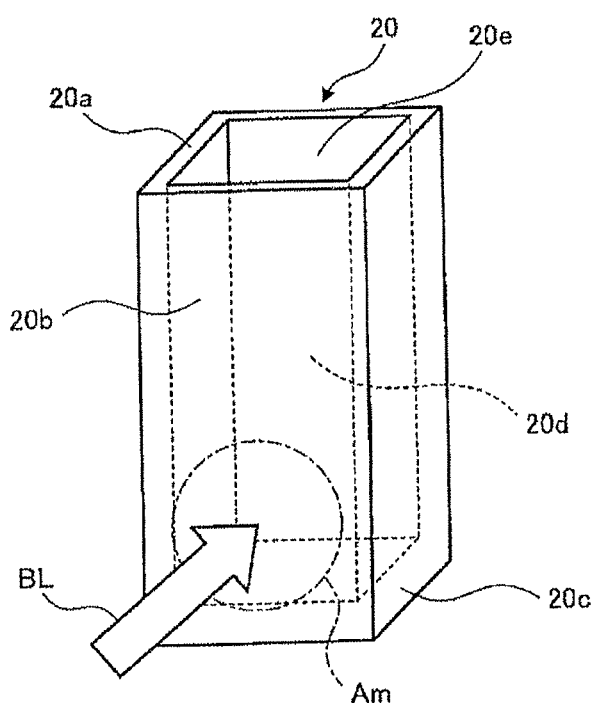
FIG. 3 is a perspective view of a reaction container 20.

Next, the photometry section 18 and the reaction container 20 will be described. FIG. 2 is a schematic view illustrating a diagrammatic configuration of the photometry section 18. FIG. 3 is a perspective view of the reaction container 20. As illustrated in FIG. 2, the photometry section 18 comprises: a light source 18a; a light receiving section 18b; and an A/D converter 18c. The light source 18a and light receiving section 18b are positioned at positions facing each other, with a reaction container 20 retained by the reaction table 13 interposed therebetween. The light source 18a is positioned on the side closer to the internal circumference of the reaction table 13. The light receiving section 18b is positioned on the side closer to the external circumference of the reaction table 13. The light source 18a is realized with a halogen lamp or the like, and irradiates light for analysis onto a reaction container 20. The light receiving section 18b comprises: a diffraction grating, such as a concave surface diffraction grating; and a light receiving sensor, such as a light receiving element array, a CCD sensor and a CMOS sensor, for measuring light separated by the diffraction grating for each spectrum determined by a measurement category, and outputting a signal corresponding to the amount of light thereof. The A/D converter 18c converts a signal output from the light receiving section 18b into a digital value, and outputs the digital value to the control section 31.

As illustrated in FIG. 3, the reaction container 20 is a very small container with a volume of, for example, several nL to several mL. A liquid retaining part 20d for retaining a liquid is formed with a side wall 20a, a side wall 20b and a bottom wall 20c, and an opening 20e lies above the liquid retaining part 20d. For the reaction container 20, a transparent material, such as glass including heat-resistant glass, or synthetic resin including cyclic olefin and polystyrene, is used to transmit 80% or more of light contained in an analysis light BL (e.g., analysis light of a wavelength in the range of 340 nm to 800 nm) irradiated from the light source 18a of the photometry section 18. The reaction container 20 is positioned such that the side wall 20b faces the radius direction of the reaction table 13. In addition, in one embodiment, when the reaction container 20 passes, with the rotation of the reaction table 13, through the analysis light BL irradiated by the light source of the photometry section 18, the bottom portion of the side wall 20b is used as a photometric region Am, through which the analysis light BL passes. The shape of the reaction container 20 can be in such a manner not to cause variation in the measurement of absorbance at a plurality of points of the reaction container 20. The shape need not be in a cuboid shape as illustrated in FIG. 3, and it is sufficient enough when two faces, on which the analysis light is irradiated, are parallel to each other among the side walls of the reaction container.

Figure 4:
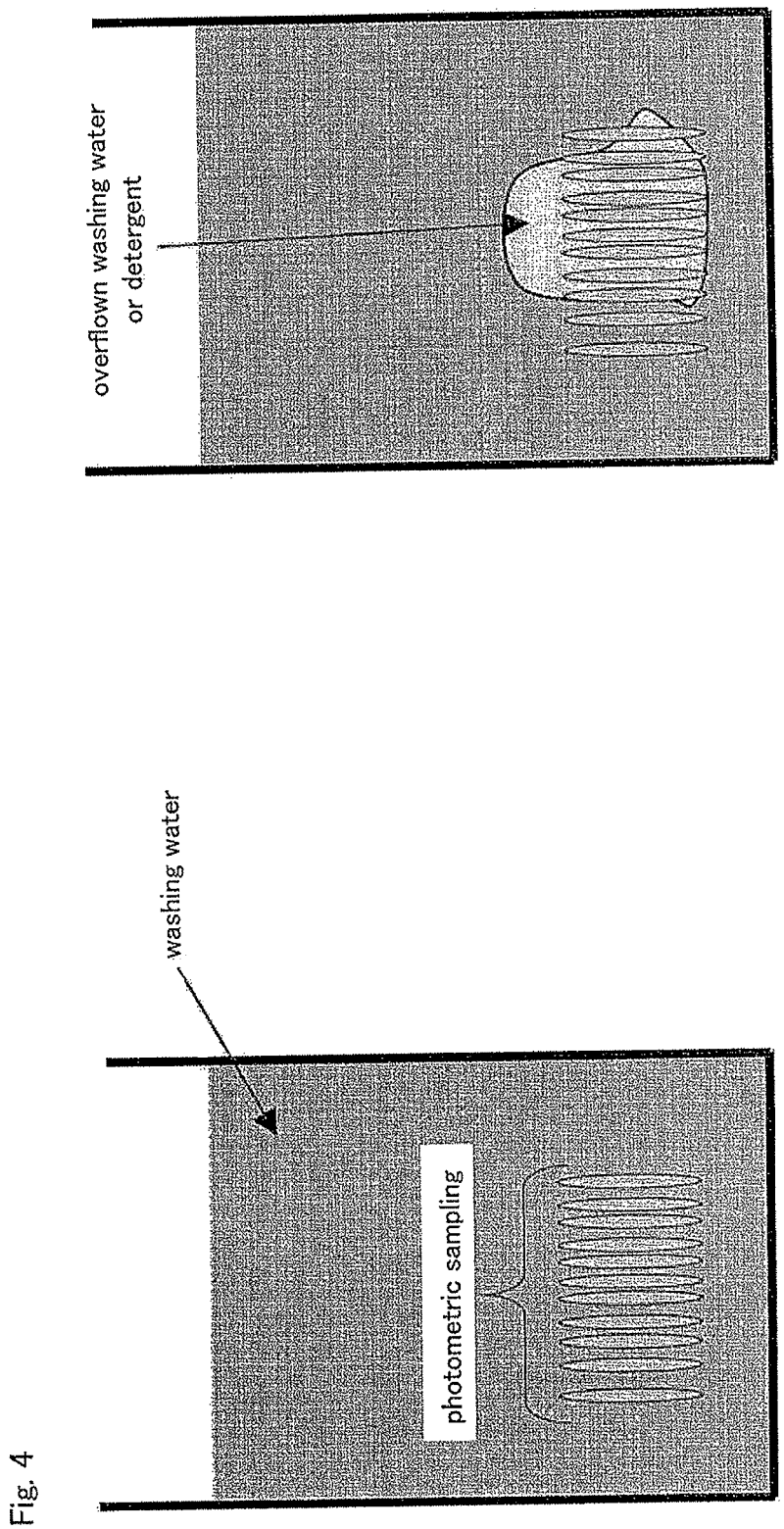
FIG. 4 is a schematic view of reaction containers 20 at a normal time (left figure: when there is no liquid overflow)

FIG. 4 is a schematic view illustrating reaction containers 20 at a normal time (left figure: when there is no liquid overflow) and an abnormal time (right figure: when there is a liquid overflow) in a case when the absorbance of the liquid contained in a reaction container 20 is measured at eleven points in the reaction container 20 while the reaction container 20 passes through the photometry section 18 once. Each of the elongated regions for the photometric sampling in FIG. 4 corresponds to a portion at which the absorbance of the liquid is measured. During the normal time, since washing water or detergent is not attached to the face for photometry, variation in photometric sampling data is small, and the standard deviation of absorbance is small. Since the variation in photometric sampling data during the normal time is due to the influence of a stain or scratch on the face for photometry, this standard deviation of the absorbance will be a value unique to each reaction container and to each wavelength. Accordingly, the reproducibility of the standard deviation of absorbance is high when the absorbance of the liquid in the same reaction container is measured with the same wavelength during the normal time. As such, during the normal time, since the reproducibility of the standard deviation of absorbance is high when the absorbance of the liquid in the same reaction container is measured with the same wavelength, the difference in the standard deviation of absorbance of the liquid in the same reaction container measured with the same wavelength at two different times will be small. On the other hand, since overflown washing water or detergent is attached to the face for photometry during the abnormal time, the variation of the photometric sampling data is great and the standard deviation of absorbance is great. The reason why the variation of the photometric sampling data becomes great during the abnormal time will be described using the example illustrated on the right side of FIG. 4. Although the absorbances measured by the photometric sampling at the first and second points from the left are the same as the absorbances during the normal time, the absorbances measured by the photometric sampling at the third to eleventh points will be those during the normal time with the absorbance of wash water or detergent attached to the face for photometry added thereto. Thus, the variation of the photometric sampling data becomes great during the abnormal time. Furthermore, since the variation of the photometric sampling data will vary depending on the way the overflown wash water or detergent attaches on the face for photometry, the reproducibility of the standard deviation of absorbance is low when the absorbance of the liquid in the same reaction container is measured with the same wavelength during the abnormal time as opposed to the normal time. As such, during the abnormal time, since the reproducibility of the standard deviation of absorbance is low when the absorbance of the liquid in the same reaction container is measured with the same wavelength, the difference in the standard deviation of absorbance of the liquid in the same reaction container measured with the same wavelength at two different times will be great.

In the present invention, an overflow of liquid is detected by utilizing this characteristic that the difference in the standard deviation of absorbance of the liquid in the same reaction container measured with the same wavelength at two different times is small during the normal time, and the difference in the standard deviation of absorbance of the liquid in the same reaction container measured with the same wavelength at two different times is great during the abnormal time.

Specifically, in one embodiment, the presence or absence of a liquid overflow is detected by comparing the difference in the standard deviation of absorbance of the liquid in the same reaction container measured with the same wavelength at two different times, with a predetermined threshold value. When the difference in the standard deviation is less than the predetermined threshold value, it corresponds to the normal time. Thus, no liquid overflow is judged as being present. When the difference in the standard deviation is greater than or equal to the predetermined threshold value, it corresponds to the abnormal time. Thus, liquid overflow is judged as being present.

FIG. 5 illustrates an example processing order for detecting an overflow of liquid from at least one of a plurality of reaction containers that the analyzer 1 comprises. The processing order is performed during the washing step of the reaction containers 20. In the processing order, the absorbance is measured with the same wavelength.

Step S501: At a time T1, at which a specific reaction container among a plurality of reaction containers 20 transferred on the reaction table 13, passes through the photometry section 18, the absorbance of the liquid contained in said one specific reaction container is measured at a predetermined number of points thereof by the photometry section 18.

Step S502: In the standard deviation calculating section 34a, a standard deviation of absorbance of the liquid, measured at the predetermined number of points, in said one specific reaction container at the time T1 is calculated from the absorbance measured at Step S501. The calculated standard deviation is stored on the recording section 35.

Step S503: At a time T2, at which said one specific reaction container transferred on the reaction table 13 passes through the photometry section 18 again, the absorbance of the liquid contained in said one specific reaction container is measured at the predetermined number of points thereof by the photometry section 18.

Step S504: In the standard deviation calculating section 34a, a standard deviation of absorbance of the liquid, measured at the predetermined number of points, in said one specific reaction container at the time T2 is calculated from the absorbance measured at Step S503. The calculated standard deviation is stored on the recording section 35.

Step S505: A judgment is made as to whether or not the difference between the standard deviation calculated at Step S502 and stored on the recording section 35 and the standard deviation calculated at Step S504 and stored on the recording section 35 is greater than a predetermined threshold value. Note that the predetermined threshold value is pre-stored on the recording section 35.

Step S506: If the difference in the standard deviation is judged to be greater than the predetermined threshold value at Step S505, then the judgment is made that the liquid is overflowing from at least one of the reaction containers 20.

If the liquid is judged as overflowing, the analyzer 1 may be stopped, or an alarm indicating that the liquid is overflowing may be displayed by the annunciation processing section 34d through the output section 36.

In the processing order in FIG. 5, if the difference in the standard deviation is judged to be at or less than the predetermined threshold value at Step S505, then Steps S503 to S505 may be repeated as follows: at a time T3 at which said one specific reaction container transferred on the reaction table 13 passes through the photometry section 18 again, the absorbance of the liquid contained in said one specific reaction container is measured at the predetermined number of points. Then, in the standard deviation calculating section 34a, a standard deviation of absorbance of the liquid, measured at the predetermined number of points, in said one specific reaction container at the time T3 is calculated from the measured absorbance. Then, the calculated standard deviation is stored on the recording section 35, and a judgment is made as to whether or not the difference between the standard deviation calculated with regard to the time T2 and stored on the recording section 35 and the standard deviation calculated with regard to the time T3 and stored on the recording section 35 is greater than the predetermined threshold value. If the difference is judged to be greater than the predetermined threshold value, then the process may go to Step S506. If the difference is judged to be at or less than the predetermined threshold value, then Steps S503 to S505 may be repeated.

Said one specific reaction container may be any of the plurality of reaction containers 20.

The times T1 and T2 may be any time during which the absorbance of the liquid contained in said one specific reaction container can be measured, that is, a time during which said one specific reaction container passes through the photometry section 18. The difference between the time T1 and the time T2 can also be determined optionally.

The time T2 may be a time during which said one specific reaction container first passes through the photometry section 18 after said one specific reaction container passed through the photometry section 18 at the time T1.

For example, in a case where washing step is performed in the order of a detergent washing step 1, a detergent washing step 2, a washing-water washing step 1, a washing-water washing step 2, a washing-water washing step 3, a washing-water washing step 4, a suctioning step 1, a drying step 1 and a drying step 2, the photometry step at either of Step S501 or Step S503 may be performed every time after the washing-water washing step 4. Alternatively, the photometry step at either of Step S501 or Step S503 may be performed every time after each washing step (detergent washing steps 1 to 2, and washing-water washing steps 1 to 4). The technique of performing the photometry step after the washing-water washing step 4 is advantageous in that the possibility is low for erroneous detection due to a stain or tested liquid since the state after the washing-water washing step 4 is a state where the reaction container is fully washed. The technique of performing the photometry step after each washing step is advantageous in that the detection sensitivity is increased because the part to be judged is increased.

While the absorbance is measured with the same wavelength in the processing order in FIG. 5, the absorbance may be measured with a plurality of wavelengths. However, three values used at Step S505, that is the two standard deviations and the predetermined threshold value, need to be for the same wavelength.

FIG. 6 illustrates another example of processing order for detecting an overflow of liquid from at least one of a plurality of reaction containers that the analyzer 1 comprises. This processing order is performed during the washing step for the reaction containers 20. Note that the absorbance is measured with the same wavelength in this processing order.

Step S601: At a time T1, at which a specific reaction container among a plurality of reaction containers 20 transferred on the reaction table 13, passes through the photometry section 18, the absorbance of the liquid contained in said one specific reaction container is measured at a predetermined number of points thereof by the photometry section 18.

Step S602: In the standard deviation calculating section 34a, a standard deviation of absorbance of the liquid, measured at the predetermined number of points, in said one specific reaction container at the time T1 is calculated from the absorbance measured at Step S601. The calculated standard deviation is stored on the recording section 35.

Step S603: At a time T2, at which said one specific reaction container transferred on the reaction table 13 passes through the photometry section 18 again, the absorbance of the liquid contained in said one specific reaction container is measured at the predetermined number of points thereof by the photometry section 18.

Step S604: In the standard deviation calculating section 34a, a standard deviation of absorbance of the liquid, measured at the predetermined number of points, in said one specific reaction container at the time T2 is calculated from the absorbance measured at Step S603. The calculated standard deviation is stored on the recording section 35.

Step S605: A judgment is made as to whether or not the difference between the standard deviation calculated at Step S602 and stored on the recording section 35 and the standard deviation calculated at Step S604 and stored on the recording section 35 is greater than a predetermined threshold value. Note that the predetermined threshold value is pre-stored on the recording section 35.

Step S606: At a time T3, at which another specific reaction container among the plurality of reaction containers 20 transferred on the reaction table 13, passes through the photometry section 18, the absorbance of the liquid contained in said another specific reaction container is measured at a predetermined number of points thereof by the photometry section 18.

Step S607: In the standard deviation calculating section 34a, a standard deviation of absorbance of the liquid, measured at the predetermined number of points, in said another specific reaction container at the time T3 is calculated from the absorbance measured at Step S606. The calculated standard deviation is stored on the recording section 35.

Step S608: At a time T4, at which said another specific reaction container transferred on the reaction table 13 passes through the photometry section 18 again, the absorbance of the liquid contained in said another specific reaction container is measured at the predetermined number of points thereof by the photometry section 18.

Step S609: In the standard deviation calculating section 34a, a standard deviation of absorbance of the liquid, measured at the predetermined number of points, in said another specific reaction container at the time T4 is calculated from the absorbance measured at Step S608. The calculated standard deviation is stored on the recording section 35.

Step S610: A judgment is made as to whether or not the difference between the standard deviation calculated at Step S607 and stored on the recording section 35 and the standard deviation calculated at Step S609 and stored on the recording section 35 is greater than a predetermined threshold value. Note that the predetermined threshold value is the same as the predetermined threshold value used at Step S605.

Step S611: If the difference in the standard deviation is greater than the predetermined threshold value at Step S605 and the difference in the standard deviation is greater than the predetermined threshold value at Step S610, then liquid is judged to be overflowing from at least one of the reaction containers 20.

If the liquid is judged as overflowing, the analyzer 1 may be stopped, or an alarm indicating that the liquid is overflowing may be displayed by the annunciation processing section 34d through the output section 36.

If either one of the differences in the standard deviations is judged to be at or less than the predetermined threshold value at Step S605 or Step S610, then Steps S603 to S605 and S608 to S610 may be repeated as follows: at a time T5, at which said one specific reaction container transferred on the reaction table 13 passes through the photometry section 18 again, the absorbance of the liquid contained in said one specific reaction container is measured at the predetermined number of points thereof by the photometry section 18. In the standard deviation calculating section 34a, a standard deviation of absorbance of the liquid, measured at the predetermined number of points, in said one specific reaction container at the time T5 is calculated from the measured absorbance. The calculated standard deviation is stored on the recording section 35. A judgment is made as to whether or not the difference between the standard deviation calculated with regard to the time T2 and stored on the recording section 35 and the standard deviation calculated with regard to the time T5 and stored on the recording section 35 is greater than a predetermined threshold value. At a time T6, at which said another specific reaction container transferred on the reaction table 13 passes through the photometry section 18 again, the absorbance of the liquid contained in said another specific reaction container is measured at the predetermined number of points thereof by the photometry section 18. In the standard deviation calculating section 34a, a standard deviation of absorbance of the liquid, measured at the predetermined number of points in said specific another reaction container at the time T6 is calculated from the measured absorbance. The calculated standard deviation is stored on the recording section 35. A judgment is made as to whether or not the difference between the standard deviation calculated with regard to the time T4 and stored on the recording section 35 and the standard deviation calculated with regard to the time T6 and stored on the recording section 35 is greater than a predetermined threshold value. If both of the difference in the standard deviation with regard to said one specific reaction container and the standard deviation with regard to said another specific reaction container are judged to be greater than the predetermined threshold value, then the process may go to step S611. If either of the differences is determined to be at or less than the predetermined threshold value, then Steps S603 to S605 and S608 to S610 may be repeated again.

Said one specific reaction container and said another specific reaction container may be any of the plurality of reaction containers 20. The relationship between said one specific reaction container and said another specific reaction container is also determined optionally. The relationship between said one specific reaction container and said another specific reaction container may be such that they are away from each other by only one-fifth of a revolution, or by only half of a revolution.

The times T1 and T2 may be any time at which the absorbance of the liquid contained in said one specific reaction container can be measured, that is, a time at which said one specific reaction container passes through the photometry section 18. The difference between the times T1 and T2 is also determined optionally.

The time T2 may be a time at which, said one specific reaction container first passes through the photometry section 18 after said one specific reaction container passed through the photometry section 18 at the time T1.

Similarly, the times T3 and T4 may be any time at which the absorbance of the liquid contained in said another specific reaction container can be measured, that is, a time during which said another specific reaction container passes through the photometry section 18. The difference between the times T3 and T4 is also determined optionally.

The time T4 may be a time during which said one specific reaction container first passes through the photometry section 18 after said another specific reaction container passed through the photometry section 18 at the time T3.

For example, in a case where washing step is performed in the order of a detergent washing step 1, a detergent washing step 2, a washing-water washing step 1, a washing-water washing step 2, a washing-water washing step 3, a washing-water washing step 4, a suctioning step 1, a drying step 1 and a drying step 2, the photometry step at any of Step S601, Step S603, Step S606, or Step S608 may be performed every time after the washing-water washing step 4. Alternatively, the photometry step at any of Step S601, Step S603, Step S606, or Step S608 may be performed every time after each of the washing steps (detergent washing steps 1 to 2, and washing-water washing steps 1 to 4). The technique of performing the photometry step after the washing-water washing step 4 is advantageous in that the possibility is low for erroneous detection due to a stain or tested liquid since the state after the washing-water washing step 4 is a state where the reaction container is fully washed. The technique of performing the photometry step after each washing step is advantageous in that the detection sensitivity is increased because the part to be judged is increased.

In addition, while the absorbance is measured with the same wavelength in the processing order in FIG. 6, the absorbance may be measured with a plurality of wavelengths. However, three values used at Step S605 and Step S610, that is the two standard deviations and the predetermined threshold value, need to be for the same wavelength.

In the embodiment illustrated in FIG. 6, it becomes possible to reduce the possibility of causing erroneous judgment that can occur in the embodiment illustrated in FIG. 5 because of the difference in the standard deviation being at or more than the predetermined threshold value due to reasons other than liquid overflowing (such as a reason that air bubbles in a reaction container moved in between the time T1 and the time T2). Since it is extremely hard for the difference in the standard deviation to be at or more than the predetermined threshold value due to reasons other than liquid overflowing, the possibility is extremely low for such an extremely rare case to occur twice consecutively. Thereby, it becomes possible to reduce the possibility of causing erroneous judgment.

In the embodiment illustrated in FIG. 5, the liquid is judged as overflowing from at least one of the reaction containers 20 based on the judgment as to whether the difference in the standard deviation with regard to one reaction container is greater than a predetermined threshold value. In the embodiment illustrated in FIG. 6, the liquid is judged as overflowing from at least one of the reaction containers 20 based on the judgment as to whether the differences in the standard deviations with regard to two reaction containers are both greater than a predetermined threshold value. However, the number of reaction containers used for the judgment that liquid is overflowing from the reaction container is not limited to one or two in the embodiments illustrated in FIGS. 5 and 6. The number of such reaction containers may be three or more.

While the analyzer 1 is described that has a configuration in which the reaction containers 20 are arranged in a circle and they are transferred along the circumference on the reaction table 13, this configuration is for explanatory purpose only and the present invention is not limited to the subject configuration. In the present invention, the reaction container to be measured or the photometry section 18 may be configured to be movable such that the reaction container to be measured can be measured by the photometry section 18. It is apparent that the technique of detecting an overflowing liquid by the present invention is feasible even in such a configuration.

Furthermore, while the analyzer 1 is described that has a configuration in which the photometry section 18 and the liquid overflow detecting section 34 are away from each other, this configuration is for explanatory purpose only and the present invention is not limited to the subject configuration. In the present invention, the photometry section 18 and the liquid overflow detecting section 34 may be configured as one apparatus referred to as a detection apparatus. It is apparent that the technique of detecting an overflowing liquid by the present invention is feasible even in such a configuration.

The predetermined threshold values used in the embodiments illustrated in FIGS. 5 and 6 are predetermined threshold values, and they are stored on the recording section 35. Hereinafter, with regard to the embodiment illustrated in FIG. 6, an example of a method for determining such a threshold value will be described.

The predetermined threshold value is calculated by collecting a sufficient amount of standard deviation data (data of the difference in the standard deviation calculated at Step S604 and Step S609 in the embodiment illustrated in FIG. 6) and based on the data and the probability of the occurrence of erroneous detection.

If the frequency for the apparatus to make erroneous detection is set to be once during the seven-year life of the apparatus, the probability is as follows: if 1,000 tests are conducted per unit per hour for five hours a day and twenty-five days a month, the following is provided:
total tests: 5 (hour/day)×1,000 (test/time/unit)×25 (day/month)×12 (month/year)×7 (years)=10,500,000 tests/unit, and thus
probability of erroneous detection: $1/10{,}500{,}000 \approx 9.52 \times 10^{-8}$.

Specifically, it means that the probability for the difference in the standard deviation to exceed the threshold value twice consecutively in the embodiment illustrated in FIG. 6 is $9.52 \times 10^{-8}$.

In this case, the probability for the difference in the standard deviation to exceed the threshold value once is calculated utilizing the binomial distribution.

Where the probability of a certain event is defined as p, the probability P(x) of the event occurring x times when the trial is conducted n times, is, in general, $P(x) = {}_nC_x p^x (1-p)^{n-x}$ (formula I), according to the binomial distribution.

Under the circumstance considered herein, the denotation p corresponds to the probability of the difference in the standard deviation exceeding a threshold value once during a normal time, and the denotation P(x) corresponds to the probability of the difference in the standard deviation exceeding a threshold value twice consecutively. Accordingly, a P(x) of about $9.52 \times 10^{-8}$ is obtained. The denotation n corresponds to the number of judgment, and in this case is 2. The denotation x corresponds to the number of events exceeding the threshold value, and in this case is 2.

When these values are substituted into the above-mentioned (formula I), a probability of $p=309 \times 10^{-6}$ is obtained. Accordingly, the threshold value is at the position of the probability p obtained above, in the data of the difference in the standard deviation. That is, when there are a million data, the predetermined threshold value is determined as the value of the 309th difference from the maximum value of the difference.

While the case of the embodiment illustrated in FIG. 6 has been described herein, the predetermined threshold value can be obtained in a similar manner in the case of other embodiments.

As described above, the present invention is exemplified by the use of its preferred embodiments. However, the present invention should not be interpreted solely based on the embodiments described above. It is understood that the scope of the present invention should be interpreted solely based on the claims. It is also understood that those skilled in the art can implement equivalent scope of technology, based on the description of the present invention and common knowledge from the description of the detailed preferred embodiments of the present invention.

DESCRIPTION OF THE REFERENCE NUMERALS

1 analyzer
2 measurement mechanism
3 control mechanism
11 sample transferring section
11a sample container
11b sample rack
12 sample dispensing mechanism
13 reaction table
14 reagent repository
15 reagent container
17 stirring section
18 photometry section
19 washing section
20 reaction container
31 control section
32 input section
33 analysis section
34 liquid overflow detecting section
34a standard deviation calculating section
34b standard deviation judging section
34c liquid overflow judging section
34d annunciation processing section
35 recording section
36 output section
37 transmission and reception section

The invention claimed is:

1. A method for detecting liquid overflowing from at least one of a plurality of containers in an analyzer, each container containing liquid, the method comprising the steps of:
for each one of N-number of containers among the plurality of containers,
measuring, by a photometry section having a light source and a light receiving section of the analyzer, an absorbance of the liquid contained in the one container at a plurality of spatially separated points of the one container at a first time corresponding to the one container;
calculating a standard deviation of the absorbance of the liquid measured at the plurality of spatially separated points of the one container at the first time corresponding to the one container, as a first standard deviation;
measuring an absorbance of the liquid contained in the one container at the plurality of spatially separated points at a second time corresponding to the one container;
calculating a standard deviation of the absorbance of the liquid measured at the plurality of spatially separated points of the one container at the second time corresponding to the one container, as a second standard deviation; and
comparing a difference between the first standard deviation and the second standard deviation, with a predetermined threshold value associated with liquid overflow; and
judging that the liquid is overflowing from at least one of the plurality of containers by obtaining the difference between the first standard deviation and the second standard deviation, and determining that the difference is greater than the predetermined threshold value in the step of comparing for all of the N-number of containers, wherein the liquid contained in the plurality of containers is detergent or wash water, wherein the method further comprises:
the step of displaying an alarm indicating that the liquid is overflowing when the liquid is judged as overflowing from at least one of the plurality of containers.

2. The method according to claim 1, further comprising the step of stopping the analyzer when the liquid is judged as overflowing from at least one of the plurality of containers.

3. The method according to claim 1, wherein the steps of measuring the absorbance are performed every time after a same washing process.

4. The method according to claim 1, wherein the steps of measuring the absorbance are performed every time after each washing process.

5. The method of claim 1,
wherein calculating the standard deviation of the absorbance of the liquid measured at the plurality of spatially separated points of the one container at the first time corresponding to the one container, as the first standard deviation is performed by the standard deviation calculating section of the analyzer;
wherein measuring the absorbance of the liquid contained in the one container at the plurality of spatially separated points at the second time corresponding to the one container is performed by the photometry section of the analyzer;
wherein calculating the standard deviation of the absorbance of the liquid measured at the plurality of spatially separated points of the one container at the second time corresponding to the one container, as the second standard deviation is performed by the standard deviation calculating section of the analyzer; and
wherein comparing the difference between the first standard deviation and the second standard deviation, with the predetermined threshold value associated with liquid overflow is performed by a standard deviation judging section of the analyzer; and wherein judging that the liquid is overflowing from at least one of the plurality of containers by obtaining the difference between the first standard deviation and the second standard deviation, and determining that the difference is greater than the predetermined threshold value in the step of comparing for all of the N-number of containers is performed by a liquid overflow judging section of the analyzer.

6. A method for detecting liquid overflowing from at least one of a plurality of containers in an analyzer, each container containing liquid, the method comprising the steps of:
for each one of N-number of containers among the plurality of containers,
measuring, by a photometry section having a light source and a light receiving section of the analyzer, an absorbance of the liquid contained in the one container at a plurality of spatially separated points of the one container at a first time corresponding to the one container;
calculating a standard deviation of the absorbance of the liquid measured at the plurality of spatially separated points of the one container at the first time corresponding to the one container, as a first standard deviation;
measuring an absorbance of the liquid contained in the one container at the plurality of spatially separated points at a second time corresponding to the one container;
calculating a standard deviation of the absorbance of the liquid measured at the plurality of spatially separated points of the one container at the second time corresponding to the one container, as a second standard deviation; and
comparing a difference between the first standard deviation and the second standard deviation, with a predetermined threshold value associated with liquid overflow; and
judging that the liquid is overflowing from at least one of the plurality of containers by obtaining the difference between the first standard deviation and the second standard deviation, and determining that the difference is greater than the predetermined threshold value in the step of comparing for all of the N-number of containers, wherein the steps of measuring the absorbance use a plurality of wavelengths, wherein the method further comprises:
displaying an alarm indicating that the liquid is overflowing when the liquid is judged as overflowing from at least one of the plurality of containers.

7. The method of claim 6,
wherein calculating the standard deviation of the absorbance of the liquid measured at the plurality of spatially separated points of the one container at the first time corresponding to the one container, as the first standard deviation is performed by the standard deviation calculating section of the analyzer;
wherein measuring the absorbance of the liquid contained in the one container at the plurality of spatially separated points at the second time corresponding to the one container is performed by the photometry section of the analyzer;
wherein calculating the standard deviation of the absorbance of the liquid measured at the plurality of spatially separated points of the one container at the second time corresponding to the one container, as the second standard deviation is performed by the standard deviation calculating section of the analyzer; and wherein comparing the difference between the first standard deviation and the second standard deviation, with the predetermined threshold value associated with liquid overflow is performed by a standard deviation judging section of the analyzer; and
wherein judging that the liquid is overflowing from at least one of the plurality of containers by obtaining the difference between the first standard deviation and the second standard deviation, and determining that the difference is greater than the predetermined threshold value in the step of comparing for all of the N-number of containers is performed by a liquid overflow judging section of the analyzer.

8. A detection apparatus for detecting that liquid is overflowing from at least one of a plurality of containers in an analyzer, each container containing the liquid, the detection apparatus comprising:
a section for measuring, for each one of N-number of containers among the plurality of containers, an absorbance of the liquid contained in the one container at a plurality of spatially separated points of the one container at a first time corresponding to the one container;
a section for calculating a standard deviation of the absorbance of the liquid measured at the plurality of spatially separated points of the one container at the first time corresponding to the one container, as a first standard deviation;
a section for measuring an absorbance of the liquid contained in the one container at the plurality of spatially separated points at a second time corresponding to the one container;
a section for calculating a standard deviation of the absorbance of the liquid measured at the plurality of spatially separated points of the one container at the second time corresponding to the one container, as a second standard deviation; and
a section for comparing a difference between the first standard deviation and the second standard deviation, with a predetermined threshold value associated with liquid overflow;
a section for judging that the liquid is overflowing from at least one of the plurality of containers by obtaining the difference between the first standard deviation and the second standard deviation, and determining that the difference is greater than the predetermined threshold value in the step of comparing for all of the N-number of containers, wherein the liquid contained in the plurality of containers is detergent or wash water; and
a section for displaying an alarm indicating that the liquid is overflowing when the liquid is judged as overflowing from at least one of the plurality of containers.

9. The detection apparatus of claim 8,
wherein calculating the standard deviation of the absorbance of the liquid measured at the plurality of spatially separated points of the one container at the first time corresponding to the one container, as the first standard deviation is performed by the standard deviation calculating section of the analyzer;
wherein measuring the absorbance of the liquid contained in the one container at the plurality of spatially separated points at the second time corresponding to the one container is performed by a photometry section of the analyzer;
wherein calculating the standard deviation of the absorbance of the liquid measured at the plurality of spatially separated points of the one container at the second time corresponding to the one container, as the second standard deviation is performed by the standard deviation calculating section of the analyzer; and wherein comparing the difference between the first standard deviation and the second standard deviation, with the predetermined threshold value associated with liquid overflow is performed by a standard deviation judging section of the analyzer; and wherein judging that the liquid is overflowing from at least one of the plurality of containers by obtaining the difference between the first standard deviation and the second standard deviation, and determining that the difference is greater than the predetermined threshold value in the step of comparing for all of the N-number of containers is performed by a liquid overflow judging section of the analyzer.

10. A method for detecting liquid overflowing from at least one of a plurality of containers in an analyzer, each container containing liquid, the method comprising the steps of:

for each one of N-number of containers among the plurality of containers,
  measuring, by a photometry section having a light source and a light receiving section of the analyzer, an absorbance of the liquid contained in the one container at a plurality of spatially separated points of the one container at a first time corresponding to the one container;
  calculating a standard deviation of the absorbance of the liquid measured at the plurality of spatially separated points of the one container at the first time corresponding to the one container, as a first standard deviation;
  measuring an absorbance of the liquid contained in the one container at the plurality of spatially separated points at a second time corresponding to the one container;
  calculating a standard deviation of the absorbance of the liquid measured at the plurality of spatially separated points of the one container at the second time corresponding to the one container, as a second standard deviation; and
  comparing a difference between the first standard deviation and the second standard deviation, with a predetermined threshold value associated with liquid overflow; and judging that the liquid is overflowing from at least one of the plurality of containers by obtaining the difference between the first standard deviation and the second standard deviation, and determining that the difference is greater than the predetermined threshold value in the step of comparing for all of the N-number of containers, wherein each container comprises a synthetic resin including a cyclic olefin and polystyrene, wherein the method further comprises:

displaying an alarm indicating that the liquid is overflowing when the liquid is judged as overflowing from at least one of the plurality of containers.

11. The method of claim 10, wherein calculating the standard deviation of the absorbance of the liquid measured at the plurality of spatially separated points of the one container at the first time corresponding to the one container, as the first standard deviation is performed by the standard deviation calculating section of the analyzer;

wherein measuring the absorbance of the liquid contained in the one container at the plurality of spatially separated points at the second time corresponding to the one container is performed by the photometry section of the analyzer;

wherein calculating the standard deviation of the absorbance of the liquid measured at the plurality of spatially separated points of the one container at the second time corresponding to the one container, as the second standard deviation is performed by the standard deviation calculating section of the analyzer; and wherein comparing the difference between the first standard deviation and the second standard deviation, with the predetermined threshold value associated with liquid overflow is performed by a standard deviation judging section of the analyzer; and wherein judging that the liquid is overflowing from at least one of the plurality of containers by obtaining the difference between the first standard deviation and the second standard deviation, and determining that the difference is greater than the predetermined threshold value in the step of comparing for all of the N-number of containers is performed by a liquid overflow judging section of the analyzer.

* * * * *